United States Patent [19]
Walinsky et al.

[11] Patent Number: 5,716,389
[45] Date of Patent: Feb. 10, 1998

[54] CARDIAC ABLATION CATHETER ARRANGEMENT WITH MOVABLE GUIDEWIRE

[76] Inventors: Paul Walinsky, 8910 Carlisle Rd., Wyndmoor, Pa. 19038-7412; Arnold Jack Greenspon, 410 Cedarwood La., Elkins Park, Pa. 19027; Arye Rosen, 508 Heartwood Rd., Cherry Hill, N.J. 08003

[21] Appl. No.: 559,816

[22] Filed: Nov. 13, 1995

[51] Int. Cl.$^6$ ............................... A61N 1/05; A61B 5/04
[52] U.S. Cl. ........................ 607/122; 128/642; 128/772
[58] Field of Search ........................... 128/642, 772; 606/34–35, 40; 604/256, 280, 282; 607/101, 116, 122

[56] References Cited

U.S. PATENT DOCUMENTS

| | | | |
|---|---|---|---|
| 4,896,671 | 1/1990 | Cunningham et al. | 128/642 |
| 4,957,110 | 9/1990 | Vogel et al. | 128/642 |
| 5,228,441 | 7/1993 | Lundquist | 128/642 |
| 5,395,328 | 3/1995 | Ockuby et al. | 128/772 X |
| 5,517,989 | 5/1996 | Frisbie et al. | 128/642 |
| 5,549,109 | 8/1996 | Samson et al. | 128/642 |
| 5,551,426 | 9/1996 | Hummel et al. | 607/122 X |

*Primary Examiner*—Francis Jaworski
*Attorney, Agent, or Firm*—William H. Meise

[57] ABSTRACT

The catheter sensing and ablation arrangement allows location and cardiac abalation on a patient. The arrangement includes an electrically nonconductive catheter body, with a guide-wire lumen. The guidewire is electrically conductive, and, when the guidewire is assembled with the catheter, extends through the lumen, and is slideable therein. The guidewire has an enlarged distal end which, when retracted, blocks the guidewire lumen. The distal end of the catheter body has an exposed first electrode, which is connected to a terminal located near the proximal end. An action potential sensor is adapted for, in a sensing mode of operation, coupling to the proximal end of the guide wire and to the electrical terminal, for sensing action potentials appearing between the enlarged end of the guide wire and the first electrode, so the end of the guide wire may be moved to a cardiac location identifiable by the action potentials. An electrically conductive contact plate is adapted for, in a second mode of operation of the sensing and ablation arrangement, being located on the exterior of the patient's back. An RF signal generator is provided for, in an ablation mode of operation, causing RF energy to be guided to the selected cardiac location, for causing current flow between the contact plate and the enlarged distal end of the guidewire, resulting in ablation of cardiac material at the cardiac location, but not at the contact plate.

17 Claims, 5 Drawing Sheets

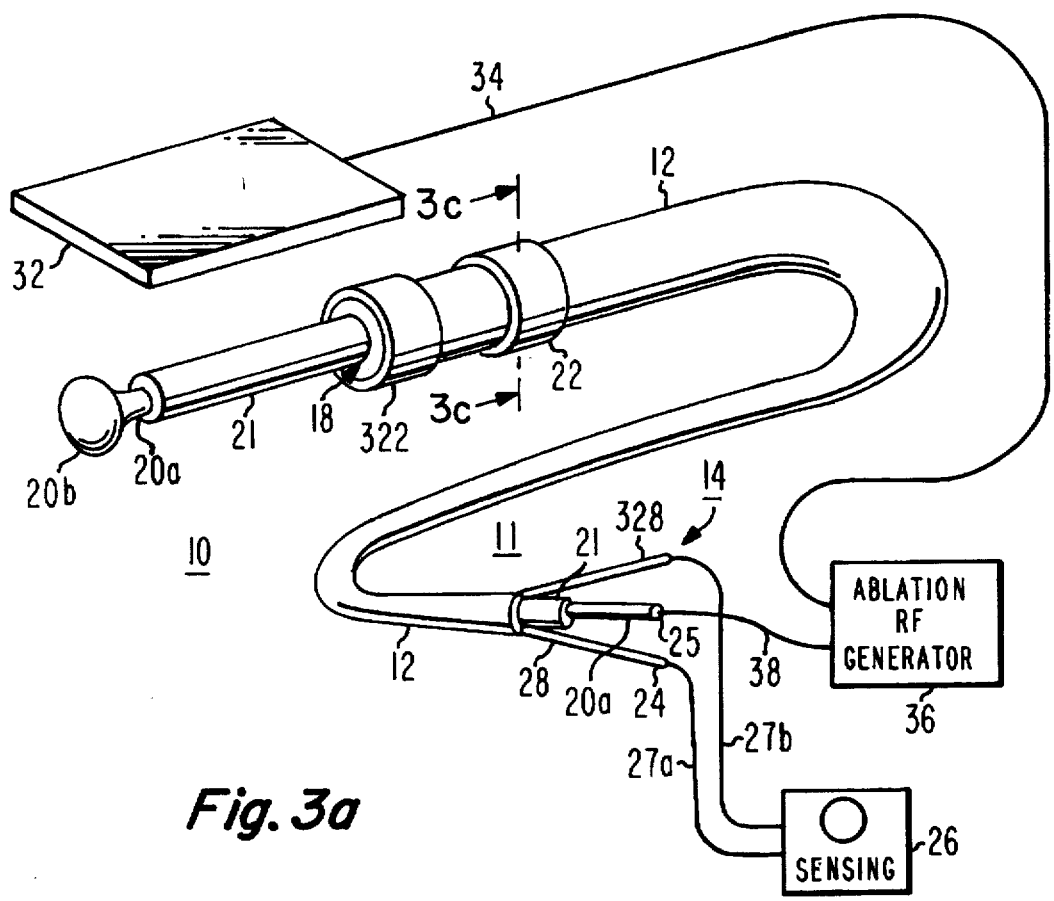
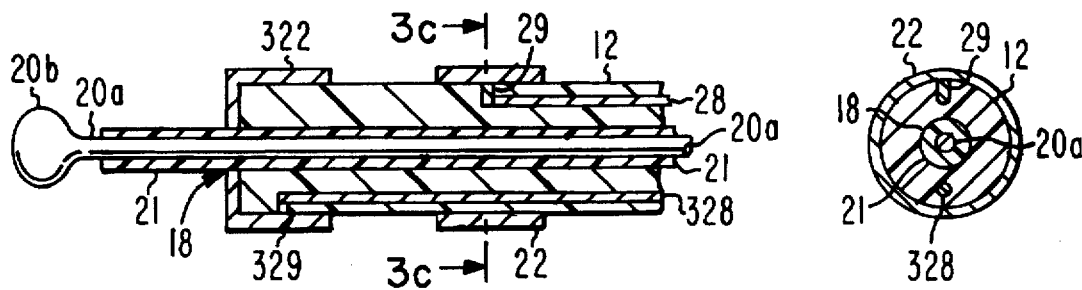 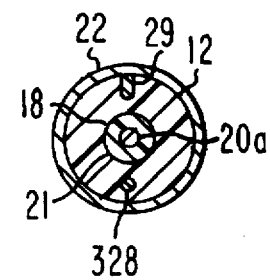
Fig. 3a
Fig. 3b            Fig. 3c

5,716,389

CARDIAC ABLATION CATHETER ARRANGEMENT WITH MOVABLE GUIDEWIRE

FIELD OF THE INVENTION

This invention relates to catheters, and more particularly to catheters for cardiac ablation.

BACKGROUND OF THE INVENTION

U.S. Pat. No. 4,641,649, issued Feb. 10, 1987 in the name of Walinsky et al. describes a catheter and method for cardiac ablation. As described therein, the symptoms of tachycardia or cardiac disrhythmya may require destruction of tissue on the interior surface of the heart, as for example to the bundle of His, an aberrant conducting fiber tract, or to the ectopic focus. As described in the abovementioned patent, the catheter used for this purpose includes a coaxial transmission line terminating in an antenna or probe. The method therein described is to insert the coaxial transmission line transluminally into the heart, and then to adjust the location of the probe by observing action potentials which appear between the probe and an exposed electrode on the exterior of the distal end of the catheter body.

It has been found that it may under some circumstances be difficult to introduce the catheter from a great vessel into the heart in order to find the appropriate location for ablation with the apparatus of the Walinsky et al. patent, because the coaxial transmission line tends to be more stiff than a similar catheter without an outer conductor. An improved catheter for ease of use in entering the heart and for sensing and ablating is desired.

SUMMARY OF THE INVENTION

The sensing and ablation arrangement according to the invention allows location and cardiac ablation on a patient. The sensing and ablation arrangement includes:

(A) an electrically nonconductive elongated catheter body defining proximal and distal ends; the catheter body including
  (a) a guide-wire lumen extending from a location near the proximal end to the distal end of the catheter body, the guide-wire lumen having a particular transverse dimension throughout a principal portion of its length which is selected to accommodate a guide wire, the guide-wire lumen also having a predetermined diameter at the distal end, which is no less than the particular transverse dimension of the guide-wire lumen;
  (b) an exposed electrically conductive first electrode located near the distal end of the catheter body;
  (c) an electrical terminus arrangement located near the proximal end of the catheter body, for making electrical connections thereto; and
  (d) an elongated electrical conducting arrangement extending from the electrical terminus arrangement to the first electrode, and in galvanic electrical communication therewith; the catheter further comprising:

(B) an electrically conductive guide wire longer than the catheter body, the guide wire including an elongated body portion extending through the guide-wire lumen of the catheter in a manner axially movable in relation thereto, and in a manner such that the guide wire and the catheter body can be completely separated from each other, the guide wire further comprises an enlarged distal end portion larger than the predetermined diameter, whereby the distal end of the guide-wire lumen is occluded when the guide-wire is fully retracted with the enlarged distal end portion abutting the distal end of the guide-wire lumen;

(C) an action potential sensing arrangement adapted for, in a sensing mode of operation of the sensing and ablation arrangement, being coupled to the proximal end of the guide wire and to the electrical terminus arrangement, for sensing action potentials appearing between the enlarged end portion of the guide wire and the first electrode, whereby the enlarged end portion of the guide wire may be moved to a cardiac location identifiable by the action potentials;

(D) an electrically conductive contact plate adapted for, in a second mode of operation of the sensing and ablation arrangement, being located adjacent to, and in contact with, the exterior of the patient;

(E) an RF signal generating arrangement adapted for, in an ablation mode of operation of the sensing and ablation arrangement, being coupled to the proximal end of the guide wire and to the contact plate, for causing RF signal energy to be guided to the cardiac location, for causing RF current to flow between the contact plate and the enlarged distal end portion of the guidewire at the cardiac location, resulting in ablation of cardiac material at the cardiac location, but not at the contact plate. In a particular embodiment of the invention, at least a distal portion of the body portion of the guide wire is surrounded by electrical insulation, leaving at least a distal portion of the enlarged distal end portion of the guide wire exposed. This arrangement is advantageous by comparison with the prior art, in that the catheter itself is not as stiff as a correspondingly thick coaxial catheter, and so is more readily moved to the desired location. In addition, the axially movable, electrically conductive guidewire allows the guidewire to be extended distally beyond the distal end of the catheter body, and it is much more flexible than the prior-art coaxial cable with nonmovable center conductor, which would otherwise have to be introduced as an entirety into the same region as the distal end of the guidewire alone. Once the proper location of the distal end of the guidewire is determined, the application of RF power (RF signal) between the distal end of the guidewire and the large contact plate keeps the power density low enough at the contact plate so that ablation occurs essentially only at the distal end of the guidewire.

A method according to the invention includes the steps of:

(A) inserting, into a vas communicating with the heart of a patient, a catheter arrangement, including
  (i) an electrically nonconductive elongated first catheter body defining proximal and distal ends; the first catheter body including
    (a) a guide-wire lumen extending from a location near the proximal end to the distal end of the first catheter body, the guide-wire lumen having a particular transverse dimension throughout a principal portion of its length which is selected to accommodate a guide wire, the guide-wire lumen also having a predetermined diameter at the distal end, which is no smaller than the particular transverse dimension of the guide-wire lumen;
    (b) an exposed electrically conductive first electrode located near the distal end of the first catheter body;

(c) an electrical terminus arrangement located near the proximal end of the first catheter body, for making electrical connections thereto; and (d) an elongated, insulated, electrical conducting arrangement extending from the electrical terminus arrangement to the first electrode, and in galvanic electrical communication therewith; the catheter arrangement further including:

(ii) an electrically conductive guide wire longer than the first catheter body, the guide wire including an elongated body portion extending through the guidewire lumen of the first catheter body in such a manner as to allow axial motion in relation thereto, and in a manner such that the guide wire and the first catheter body can be completely separated from each other, the guide wire further comprising an enlarged distal end portion larger than the predetermined diameter, whereby the distal end of the guide-wire lumen is occluded when the guide-wire is fully retracted with the enlarged distal end portion abutting the distal end of the guide-wire lumen;

(B) advancing the guide wire through the vas into the heart of the patient;

(C) advancing the catheter over the guidewire into the heart;

(D) with the action potential sensing arrangement connected to the proximal end of the guide wire and to the electrical terminus arrangement, observing the action potentials;

(E) while observing the action potentials, moving the catheter arrangement to a location at which the enlarged end portion of the guide wire is in contact with a particular cardiac location identifiable by the action potentials as one to be ablated;

(F) locating an electrically conductive plate, with a surface area at least ten times that of the distal end of the guide wire, adjacent to, and in close proximity to with, the thorax of the patient;

(G) connecting an RF generating arrangement to the proximal end of the guide wire and to the electrically conductive plate, for causing RF signal energy to be guided to the cardiac location, for causing RF current to flow between the cardiac location and the electrically conductive plate, resulting in ablation of cardiac material at the cardiac location, but not at the electrically conductive plate. In a particular method, the plate is placed on the back of the patient.

DESCRIPTION OF THE DRAWING

FIG. 3a is a simplified perspective or isometric view of a sensing and ablation arrangement according to the invention, in which the catheter includes two external electrodes as in FIGS. 2a and 2b, but in which both external electrodes have separate electrical connections through the catheter body to the proximal end, FIGS. 3b and 3c are longitudinal and transverse cross-sections, respectively, of the arrangement of FIG. 3a near the distal end thereof;

DESCRIPTION OF THE INVENTION

Figure 1A:
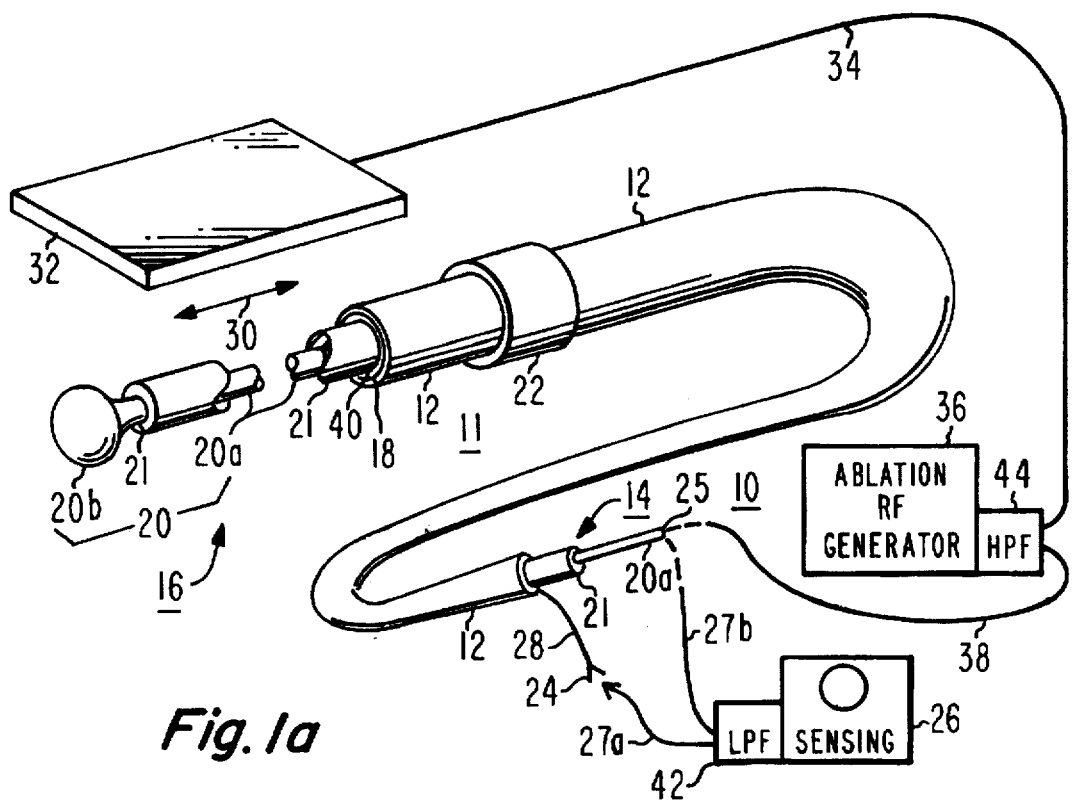
FIG. 1a is a simplified perspective or isometric representation of an action potential sensing and RF ablation arrangement according to the invention, in which a catheter includes a guidewire lumen, an external electrode, and a distal end.
Figure 1B:
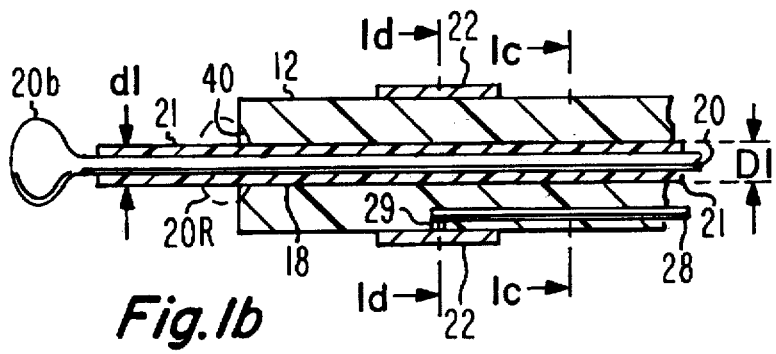
FIG. 1b is a longitudinal cross-section of a distal portion of the catheter of FIG. 1a, FIGS. 1c and 1d are transverse cross-sections of the catheter of FIG. 1a at locations 1c—1c and 1d—1d near its distal end.
Figure 1C:
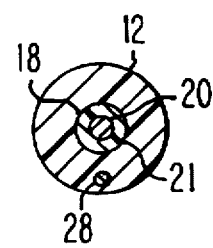
FIG. 1e is a cross-section similar to that of FIG. 1b illustrating a slightly different guidewire lumen configuration.
Figure 1D:
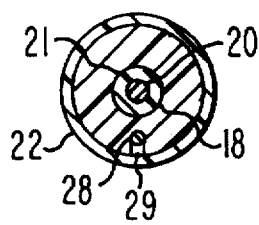
Figure 1E:
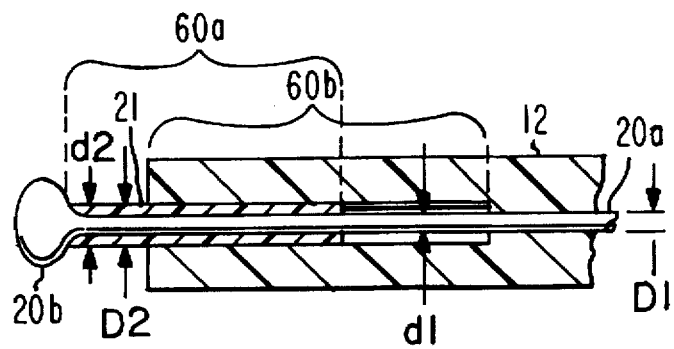

FIG. 1a is a perspective or isometric view of an action potential sensing and electrical ablation arrangement 10 according to the invention. The arrangement of FIG. 1a is intended for use in ablation of particular portions of the interior surface of the heart of a patient. In FIGS. 1a and 1b, a catheter 11 includes an elongated, flexible, electrically nonconductive body 12, which extends from a proximal end 14 to a distal end 16. Body 12 defines an elongated guidewire lumen 18 which extends from proximal end 14 to distal end 16. An electrically conductive guidewire designated generally as 20 includes an elongated body portion 20a, which is long enough to, when guidewire 20 is assembled with catheter body 12, extend through body 12, and extend beyond body 12 at both ends. Guidewire 20 also includes an enlarged end portion 20b, which may take the form of a rounded "doorknob" or "button" as illustrated. As illustrated in FIGS. 1a, 1b, and 1e, at least the most distal end of guidewire body 10a is electrically insulated by a layer, sheath or tube 21 of dielectric material, which, together with dielectric body 12, insulates the guidewire so that only enlarged end (button) portion 20b of the guidewire makes electrical contact with the body of a patient. In FIGS. 1a and 1b, the insulating sheath 21 extends all the way through the lumen 18 of body 12, and protrudes from both the proximal and distal ends. At the proximal end of catheter 11, guidewire body 20a extends beyond the end of insulating sheath 21, leaving a conductive portion of the guidewire available as a contact or terminal 25.

An annular or ring electrode 22 is affixed to catheter body 12a near the distal end 16 of catheter 11 of FIG. 1a. Electrode 22 is exposed to the exterior of the catheter, and is electrically connected to the proximal end 14 of catheter 11 by an elongated conductive wire or path 28 which extends through catheter body 12 from electrode 22 to the proximal end 14, running parallel to the guidewire lumen 18, as can be seen in FIG. 1c. At electrode 22, a radial conductive arrangement 29 connects wire 28 to electrode 22, as can best be seen in FIG. 1d.

The exterior diameter of guidewire body 20a and insulating sheath 21 is illustrated as d1 in FIG. 1b, and the interior diameter of guidewire lumen 18 of catheter body 12a is illustrated as D1. Dimensions D1 and d1 are selected, taking into consideration the materials of which they are made, so that the guidewire 20 with its insulating sheath can be moved relative to catheter body 20a, in the direction of arrows 30 of FIG. 1a. Thus, guidewire 20 can be removed completely from lumen 18, if desired. Also, the distal end of guidewire 20 can be retracted, so that the curved proximal or "rear" portion of enlarged end portion 20b of catheter 20 butts against the distal end of catheter body 12, as illustrated in FIG. 1b by dotted lines 20R (retracted). When so retracted, the curvature of the rear of enlarged end portion 20b mates with a corresponding depressed portion 40, so that the end of the guidewire lumen 18 is occluded or sealed in the fully retracted position.

In FIG. 1a, an action potential sensing arrangement is illustrated as a block 26, which includes two electrical leads 27a, 27b, which are illustrated as being connectable to proximal terminals 24 and 25 of guidewire 20 and electrode connection wire 28, respectively. Thus, in a first or sensing mode of operation of the arrangement 10 of FIG. 1a, action potentials appearing across (or between) the enlarged distal end 20b of guidewire 20 and electrode 22 can be sensed by action potential sensing arrangement 26. This sensing mode of operation allows the location of a particular portion of the heart's surface to be located, prior to operating in a second or ablation mode.

When the enlarged end portion 20b of guidewire 20 of FIG. 1a is in the proper position, as indicated by sensing block 26, sensing potentials between the enlarged end portion 20b and annular electrode 22, the guidewire is held in position. While the guidewire is held in position, ablation radio-frequency (RF) electromagnetic generator (RF signal generator) 36, if not already connected, is connected to proximal guidewire terminal 25 and to a conductive plate 32. Conductive plate 32 is in adjacent to, or preferably in contact with, the patient's thorax, and preferably his back. As is known to those skilled in the art, resistance reducing materials can be placed at the interface to aid in providing uniform contact over the surface area of the plate. The surface area of plate 32 in contact with the patient is sufficiently larger than the area of the enlarged end portion 20b of the guidewire, so that the same amount of current flowing therethrough results in a sufficiently large current density to ablate tissue at button 20b, but small enough at plate 32 to have insubstantial effect. RF generator 36 is then energized to produce a particular amount of ablation energy, by controlling the magnitude of the RF energy (power) or the duration of application of the power, or preferably both.

Those skilled in the art will recognize that, since the arrangement of FIG. 1a has two electrical instruments and three contacts, one of which is common, both the sensing and the ablation may be performed simultaneously. A low-pass filter (LPF) 42 may be used with sensing instrument 26, if desired, to reduce the amount of ablation RF signal entering sensor 26. If the impedance presented by RF generator 36 at low (action potential) frequencies is low enough to adversely affect the signal readings by action potential sensor 26, a high-pass filter (HPF) 44, presenting a high low-frequency impedance, may be coupled to generator conductors 34 and 38. Such a filter might be as simple as a capacitor coupled in series with conductor 38.

FIG. 1e is a longitudinal cross-section of the distal end of a catheter similar to that of FIGS. 1a–1d, and corresponding elements are designated by like reference numbers. In the arrangement of FIG. 1e, insulating or dielectric sheath 21 surrounds the distal end of body portion 20a of guidewire 20, but does not extend all the way to the proximal end 14 of catheter 11. Instead, sheath 21 extends only over a limited region, designated 60a in FIG. 1e, which is somewhat longer than the maximum expected distal extension of guidewire 20 from catheter body 12. Sheath 21 of FIG. 1e thus insulates all but the exposed button 20b of the guidewire, when the guidewire does not have an insulating sheath extending all the way to proximal end 14. Thus, the exterior diameter of the guidewire-and-sheath (the combination of 20a and 21) is d2 in region 60a, and the diameter of guidewire lumen 18 is D2 in corresponding region 60b. However, in regions of catheter 11 more proximal than region 60b, the guidewire body 20a has no sheath, so its diameter is d1, and the corresponding diameter of lumen 18 is D1. Thus, the diameter of lumen 18 is D1 at the proximal end, and D2 at the distal end, where D2 is greater than D1.

Figure 2A:
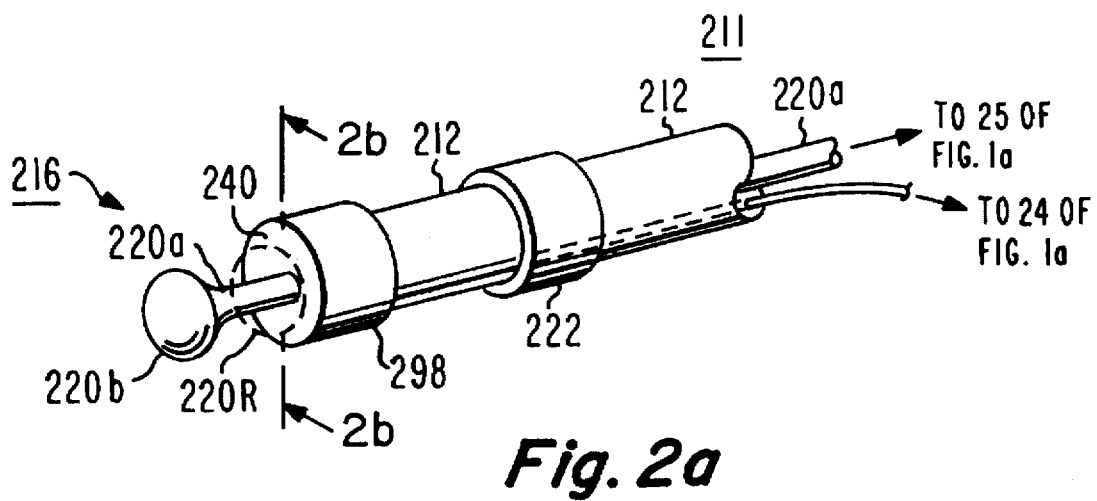
FIG. 2a is a simplified perspective or isometric view of a catheter according to the invention, in which two external electrodes are provided, and one makes contact by means of the guidewire in its retracted position.
Figure 2B:
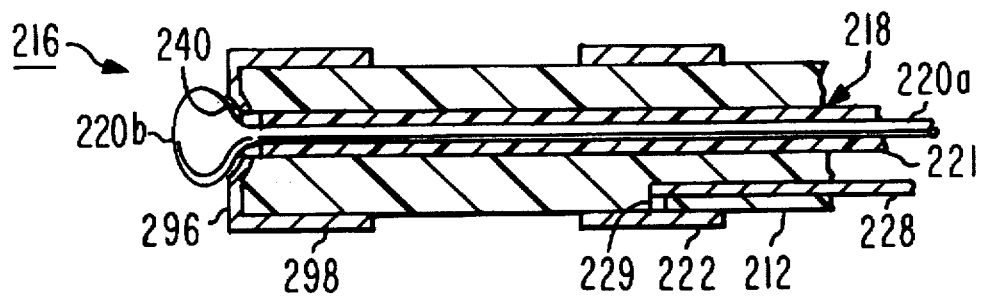
FIG. 2b is a longitudinal cross-section thereof looking in direction 2b—2b.

FIG. 2a is a simplified perspective or isometric view of a distal portion 216 of the body 212 of a catheter 211, and FIG. 2b is a longitudinal cross-section thereof looking in direction 2b—2b of FIG. 2a. Catheter 211 of FIGS. 2a and 2b may be substituted for catheter 11 in the sensing and ablation arrangement of FIGS. 1a, 1b, 1c, and 1d. In FIGS. 2a and 2b, catheter body 211 defines a guidewire lumen 218, dimensioned to accommodate a guidewire body 220a, and its sheath 221, if present, with a sliding fit. A first exposed annular electrode 222 is connected by a conductive path 229 to a wire conductor 228 extending through dielectric body 212. Wire 228 and guidewire 220 extend to terminals 24 and 25 at the proximal end of the catheter, for connection to action potential sensor 26 and RF generator 36 in place of catheter 11. Catheter 211 includes a further electrode 298 which covers a substantial portion of the distal end face 296 of catheter 211, including at least a portion of recess 240, and which also wraps around onto the cylindrical portion of body 212. This arrangement increases the effective conductive sensing surface area when the guidewire is fully retracted, because guidewire button 220b electrically contacts electrode 298. Such a larger surface area, in turn, makes it easier to perform coarse positioning of the distal end of the guidewire, before the final position of the button is established, and also increases the surface area for energy delivery for ablation.

The arrangement of FIGS. 3a and 3b is similar to that of FIGS. 1a and 1b, and corresponding elements are designated by like reference numerals. The arrangement of FIGS. 3a and 3b differs from that of FIGS. 1a and 1b in that it includes an additional external annular electrode 322, which is connected by a contact 329 and a second longitudinal wire 328 to the proximal end 14 of the catheter. The connections of action potential sensor 26 leads 27a and 27b are to wires 28 and 328, respectively, so that the action potential sensor 26 is completely isolated from RF generator 36, which is connected to plate 32 and to guidewire body 20a. FIG. 3c illustrates a transverse cross-section of the catheter of FIG. 3a, looking in direction 3c—3c.

Figure 4:
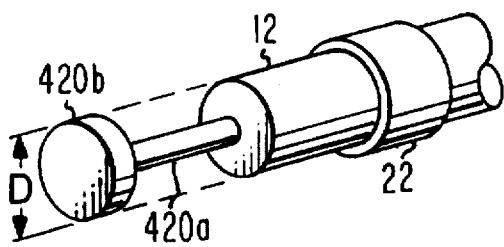
FIG. 4 is a perspective or isometric view of the distal end of a catheter according to the invention, in which the enlarged distal end of the guidewire has the same diameter as the body of the catheter.

FIG. 4 is a simplified perspective or isometric view of a catheter according to the invention, in which a guidewire includes a body portion 420a and a cylindrical "button" portion 420b defining a diameter D which equals the diameter of body portion 12 of the catheter.

Figure 5:
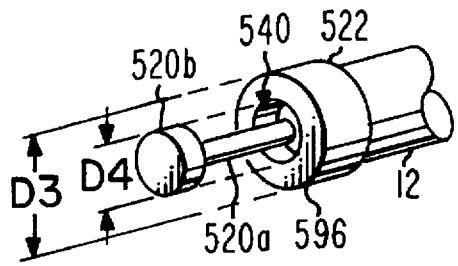
FIG. 5 is a perspective or isometric view of the distal end of a catheter according to the invention, in which the enlarged distal end of the guidewire has a smaller diameter than the body of the catheter.

FIG. 5 is a simplified perspective or isometric view of a catheter according to the invention, in which a guidewire includes a body portion 520a and a cylindrical "button" portion 520b defining a diameter D4 which is smaller than the diameter D3 of body portion 12 of the catheter. The distal end face 596 of the catheter body 12 of FIG. 5 defines a recess or cavity 540, dimensioned to accommodate button 520b both in diameter and in depth, so when the guidewire is retracted, button 520b fills cavity 540, leaving the end face flush. The catheter of FIG. 5 includes an annular electrode 522 similar to electrode 322 of FIGS. 3a and 3b.

Figure 6A:
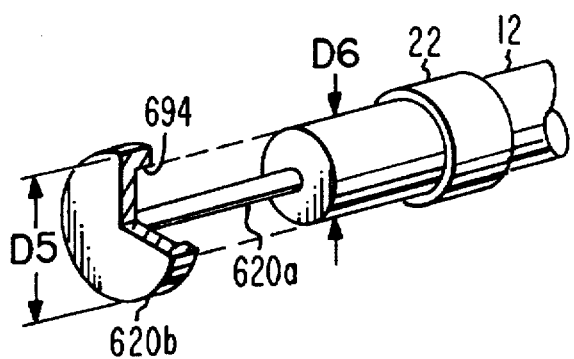
FIG. 6a is a perspective or isometric view of the distal end of a catheter according to the invention, partially cut away to reveal interior details, in which the enlarged distal end of the guidewire has a larger diameter than the body of the catheter.
Figure 6B:
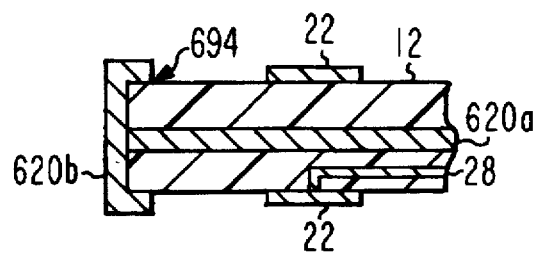
FIG. 6b is a longitudinal cross-section of the arrangement of FIG. 6A.

In the arrangement of FIGS. 6a and 6b, the guidewire includes a body portion 620a and a cylindrical button 620b defining a diameter D5 greater than the diameter D6 of the body 12 of the catheter. Button 620b defines a cavity 694, which has a diameter sufficient to accommodate the end of catheter body 12.

Figure 7A:
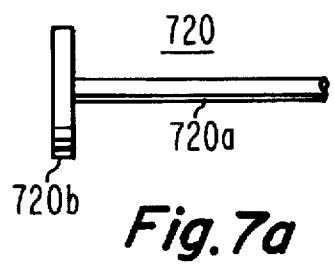
FIGS. 7a, 7b, and 7c illustrate different shapes into which an enlarged disk guidewire end can be formed.
Figure 7B:
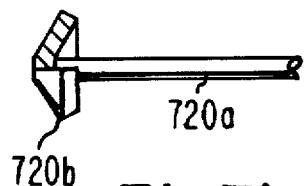
Figure 7C:
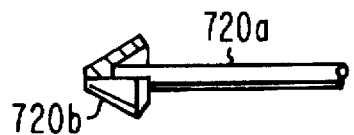

FIG. 7a is a simplified illustration of the distal end of a guidewire 720 according to the invention including a body 720a, in which the button 720b is a thin disk. In FIG 7b, the disk has been manually bent into a "parasol" shape, and in FIG. 7c, the bending has been continued past the shape of FIG. 7b. Such shapes may be convenient for various different conditions, and save cost by allowing manual shaping as conditions require, without changing catheters. The guidewire can be fully opened as in FIG. 7a, or retracted as in FIG. 7c. When fully retracted, the guidewire can be removed from the catheter and a new guidewire introduced into the catheter.

Figure 8A:
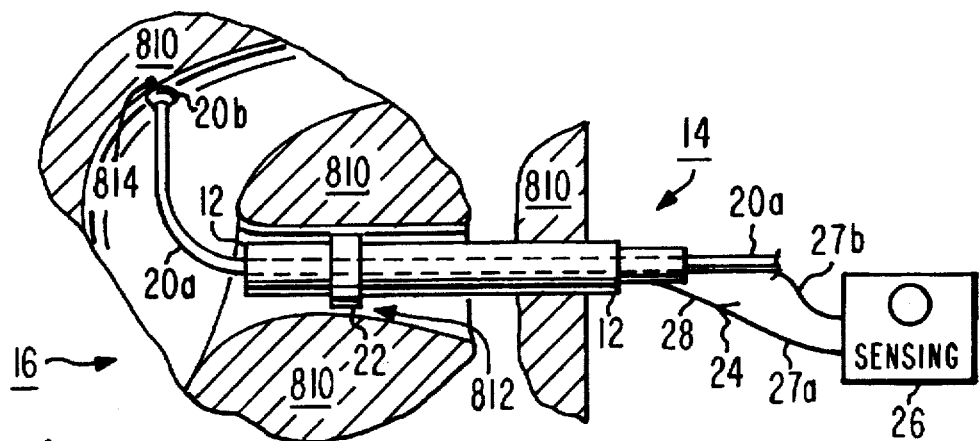
FIGS. 8a, 8b, and 8c illustrate steps in using the catheter body described in conjunction with FIGS. 1a–1e to place the guidewire in the proper location, following which a catheter body with an outer conductor of a coaxial transmission line is slipped over the in-place guidewire, to perform ablation.
Figure 8B:
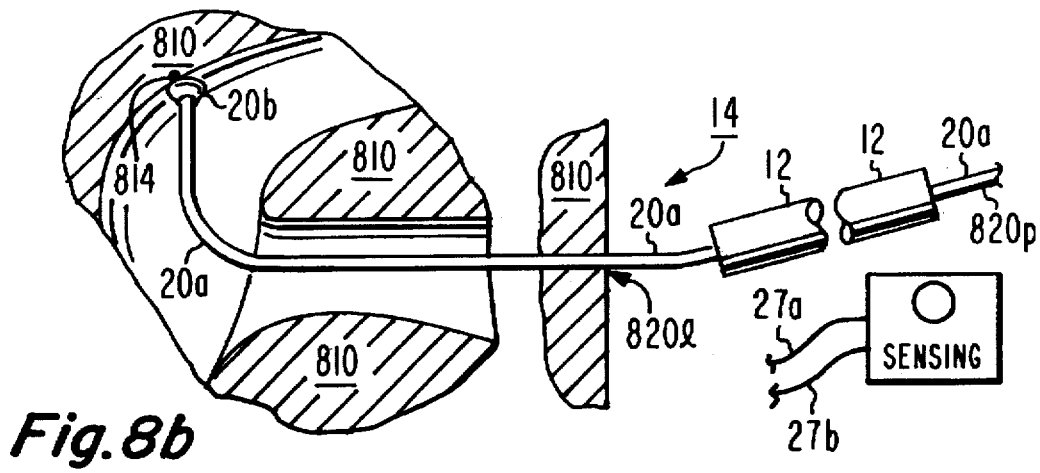
Figure 8C:
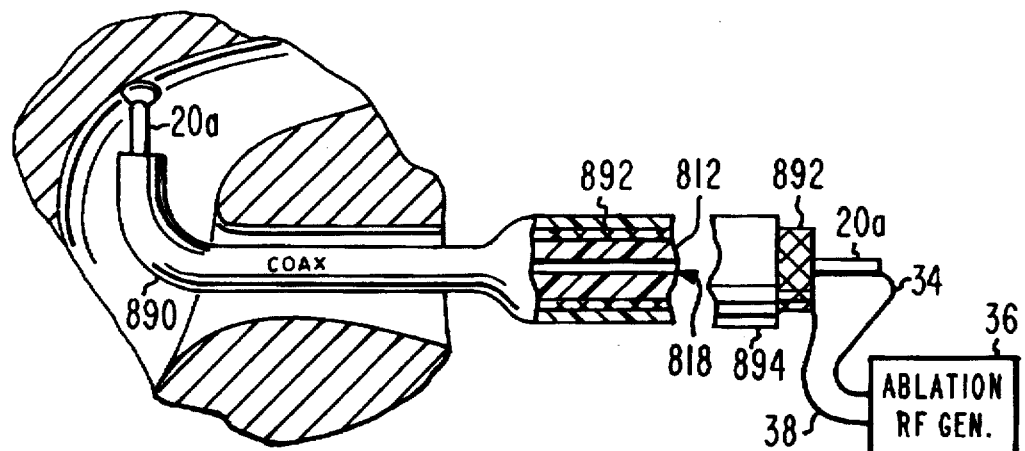

FIG. 8a illustrates a catheter arrangement, similar to that of FIG. 1a, in which the electrically conductive guidewire is in place in the body of a patient, with its enlarged distal end in contact with the desired location to be ablated. In FIG. 8a, elements corresponding to those of FIG. 1a are designated by like numerals, and 810 designates portions of the patient's heart, defining an access lumen 812 through which the catheter is brought near the region 814 to be ablated, which is located, as described above, by sensing action potentials. In FIG. 8b, the catheter body 12 has been removed from around the guidewire 20, which remains in place, in contact with point 814. It should be noted that such a removal requires the guidewire to be about twice as long as the catheter body, because maintaining the location of the guidewire requires that the guidewire be under control while the catheter body is removed. The most proximal end 820p of the guidewire is held while the body 12 of the catheter is retracted, and when the guidewire 20a is exposed at a location 8201 adjacent the patient's body, the guidewire can then be held at location 8201 adjacent the patient's body, while the catheter body 12 is removed from the remainder of the guidewire. More precisely, the length of the guidewire extending outside the patient's body must exceed the length of the catheter body to be removed by enough for two handholds to be established on the guidewire. FIG. 8c illustrates the fitting over the guidewire 20 of a second catheter body 890. The length of second catheter body 890 must be no longer than the maximum length of the body 12 which was removed, as mentioned above. Second catheter body 890 includes an elongated dielectric body portion 812 with a guidewire lumen 818, which is dimensioned to allow a sliding fit with the guidewire 20a. An electrically conductive sheath or outer conductor 892 surrounds dielectric body portion 812 along most of its length, to thereby define a coaxial transmission line when the catheter body 890 is slipped over the guidewire. A further insulative cover or sheath 894 surrounds the outer conductor 892, to prevent electrical contact between the outer conductor and the patient's body, except at the most distal location, if desired. This, then, becomes equivalent to the coaxial arrangement of the abovementioned Walinsky et al. patent, except in that the "center conductor" becomes the electrically conductive guidewire, which is axially movable within, and removable from, the remainder of the coaxial structure. With this method and arrangement, then, the guidewire can be placed in the appropriate location to be ablated more easily than the center conductor of the guidewire in prior art, because it is part of a relatively flexible, "noncoaxial-transmission-line" first catheter, and then the "noncoaxial" first catheter body can be removed from about the guidewire, leaving the guidewire in location in the patient's heart, and the stiffer coaxial catheter body can then be slipped over the guidewire, and RF ablation can then take place as described in the Walinsky et al. patent. For this purpose, RF includes microwave and other high-frequency energy.

Thus, the sensing and ablation arrangement according to the invention (10) allows location and cardiac ablation on a patient. The sensing and ablation arrangement includes:

(A) an electrically nonconductive elongated catheter body (12) defining proximal (14) and distal (16) ends; the catheter body including
  (a) a guide-wire lumen (18) extending from a location near the proximal end (14) to the distal end (16) of the catheter body (12), the guide-wire lumen (18) having a particular transverse dimension (D1) throughout a principal portion of its length which is selected to accommodate a guide wire (20), the guide-wire lumen (18) also having a predetermined diameter (D2) at the distal end, which is no less than the particular transverse dimension (D1) of the guide-wire lumen;
  (b) an exposed electrically conductive first electrode (22) located near the distal end (16) of the catheter body (12);
  (c) an electrical terminus arrangement (24) located near the proximal end of the catheter body, for making electrical connections thereto; and
  (d) an elongated electrical conducting arrangement (28) extending from the electrical terminus arrangement (24) to the first electrode (22), and in galvanic electrical communication therewith; the catheter further comprising:

(B) an electrically conductive guide wire (20) longer than the catheter body, the guide wire (20) including an elongated body portion (20a) extending through the guide-wire lumen (18) of the catheter in a manner axially movable (30) in relation thereto, and in a manner such that the guide wire (20) and the catheter body (12) can be completely separated from each other; the guide wire (20) further includes an enlarged distal end portion (20b) larger than the predetermined diameter (D2), whereby the distal end (16) of the guide-wire lumen (18) is occluded when the guide-wire (20) is fully retracted with the enlarged distal end portion (20b) abutting the distal end of the guide-wire lumen (18);

(C) an action potential sensing arrangement (26) adapted for, in a sensing mode of operation of the sensing and ablation arrangement (10), being coupled to the proximal end (14) of the guide wire (20) and to the electrical terminus arrangement (24), for sensing action potentials appearing between the enlarged end portion (20b) of the guide wire (20) and the first electrode (22), whereby the enlarged end portion (20b) of the guide wire (20) may be moved to a cardiac location identifiable by the action potentials;

(D) an electrically conductive contact plate (32) adapted for, in a second mode of operation of the sensing and ablation arrangement (10), being located adjacent to, and in contact with, the exterior of the patient;

(E) an RF signal generating arrangement (36) adapted for, in an ablation mode of operation of the sensing and ablation arrangement (10), being coupled (34, 38) to the proximal end of the guide wire (20) and to the contact plate (32), for causing RF signal energy to be guided to the cardiac location, for causing RF current to flow between the contact plate (32) and the enlarged distal end portion (20b) of the guidewire (20) at the cardiac location, resulting in ablation of cardiac material at the cardiac location, but not at the contact plate. In a particular embodiment of the invention, at least a distal portion (60) of the body portion (20a) of the guide wire (20) is surrounded by electrical insulation (21), leaving at least a distal portion of the enlarged distal end portion (20b) of the guide wire (20) exposed.

Other embodiments of the invention will be apparent to those skilled in the art. For example, while electrically insulating sheath 21 in FIGS. 1a, 1b, and 1e do not cover any portion of enlarged distal end portion 20b of the guidewire, the insulating sheath may also extend over a proximal portion of the "doorknob," to limit electrical contact to only the distal end of the enlarged portion. While the end of the guidewire has been described as having a doorknob shape, other shapes may be used, so long as they do not have contours which might cause injury to the patient.

What is claimed is:

1. A sensing and ablation arrangement for performing cardiac ablation on a patient, said sensing and ablation arrangement comprising:

(A) an electrically nonconductive elongated catheter body defining proximal and distal ends; said catheter body including
      (a) a guide-wire lumen extending from a location near said proximal end to said distal end of said catheter body, said guide-wire lumen having a particular transverse dimension throughout a principal portion of its length which is selected to accommodate a guide wire, said guide-wire lumen also having a predetermined diameter at said distal end, which may be greater than said particular transverse dimension of said guide-wire lumen;
      (b) an exposed electrically conductive first electrode located near said distal end of said catheter body; and
      (c) electrical terminus means located near said proximal end of said catheter body, for making electrical connections thereto; and
      (d) elongated electrical conducting means extending from said electrical terminus means to said first electrode, and in galvanic electrical communication therewith; said catheter further comprising:
   (B) an electrically conductive guide wire longer than said catheter body, said guide wire including an elongated body portion extending through said guide-wire lumen of said catheter in a manner axially movable in relation thereto, and in a manner such that said guide wire and said catheter body can be completely separated from each other, said guide wire further comprising an enlarged distal end portion larger than said predetermined diameter, whereby the distal end of said guide-wire lumen is occluded when said guide-wire is fully retracted with said enlarged distal end portion abutting said distal end of said guide-wire lumen;
   (C) action potential sensing means adapted for, in a sensing mode of operation of said sensing and ablation arrangement, being coupled to said proximal end of said guide wire and to said electrical terminus means, for sensing action potentials appearing between said enlarged end portion of said guide wire and said first electrode, whereby said enlarged end portion of said guide wire may be moved to a cardiac location identifiable by said action potentials;
   (D) an electrically conductive contact plate adapted for, in a second mode of operation of said sensing and ablation arrangement, being located adjacent to, and in contact with, the exterior of said patient;
   (E) RF signal generating means adapted for, in an ablation mode of operation of said sensing and ablation arrangement, being coupled to said proximal end of said guide wire and to said contact plate, for causing RF signal energy to be guided to said cardiac location, for causing RF current to flow between said contact plate and said enlarged distal end portion of said guidewire at said cardiac location, resulting in ablation of cardiac material at said cardiac location, but not at said contact plate.

2. An arrangement according to claim 1, wherein said contact plate is a back plate.

3. An arrangement according to claim 1, wherein at least a distal portion of said body portion of said guide wire is surrounded by electrical insulation, leaving at least a distal portion of said enlarged distal end portion of said guide wire exposed.

4. An arrangement according to claim 1, further comprising:

(A) a second catheter body separate from said first-mentioned catheter body, said second catheter body including a guide-wire lumen extending from a location near said proximal end to said distal end of said second catheter body, said guide-wire lumen of said second catheter body having a transverse dimension throughout a principal portion of its length which is selected to accommodate said guide wire, said guide-wire lumen of said second catheter body also having a predetermined diameter at said distal end of said second catheter body, which may be greater than said transverse dimension of said guide-wire lumen of said second catheter body;
   (B) a flexible, electrically conductive sheath electrically insulated from, and surrounding, said guide-wire lumen of said second catheter body, and extending from a location near said distal end of said second catheter body to a location near said proximal end of said second catheter body, and including electrical connection means located near said proximal end of said body of said second catheter body, for forming, in conjunction with said guide wire, an unbalanced transmission line by which said RF energy may be guided; and
   (C) electrical insulation means surrounding said sheath over a principal portion of said second catheter body, for insulating said patient from galvanic contact with said sheath.

5. A method for performing ablation on the heart of a patient, comprising the steps of:

(A) inserting, into a vas communicating with the heart of a patient, a catheter arrangement, including
      (i) an electrically nonconductive elongated first catheter body defining proximal and distal ends; said first catheter body including
         (a) a guide-wire lumen extending from a location near said proximal end to said distal end of said first catheter body, said guide-wire lumen having a transverse dimension throughout a principal portion of its length which is selected to accommodate a guide wire, said guide-wire lumen also having a predetermined diameter at said distal end, which is no smaller than said transverse dimension of said guide-wire lumen;

(b) an exposed electrically conductive first electrode located near said distal end of said first catheter body;

(c) electrical terminus means located near said proximal end of said first catheter body, for making electrical connections thereto; and (d) elongated, insulated, electrical conducting means extending from said electrical terminus means to said first electrode, and in galvanic electrical communication therewith; said catheter arrangement further comprising:

(ii) an electrically conductive guide wire longer than said first catheter body, said guide wire including an elongated body portion extending through said guide-wire lumen of said first catheter body in a manner axially movable in relation thereto, and in a manner such that said guide wire and said first catheter body can be completely separated from each other, said guide wire further comprising an enlarged distal end portion including a transverse dimension larger than said predetermined diameter, whereby the distal end of said guide-wire lumen is occluded when said guide-wire is fully, retracted with said enlarged distal end portion abutting said distal end of said guide-wire lumen;

(B) advancing said guide wire through said vas into the heart of the patient;

(C) advancing said catheter over said guidewire into said heart;

(D) connecting action potential sensing means to said proximal end of said guide wire and to said electrical terminus means, said action potential sensing means being adapted for sensing action potentials appearing between said guide wire and said first electrode;

(E) while observing said action potentials, moving said catheter arrangement to a location at which said enlarged end portion of said guide wire is in contact with a particular cardiac location identifiable by said action potentials;

(F) locating an electrically conductive plate, with a surface area at least ten times that of said distal end of said guide wire, adjacent to, and in close proximity to with, the thorax of said patient;

(G) connecting RF signal generating means to said proximal end of said guide wire and to said electrically conductive plate, for causing RF signal energy to be guided to said cardiac location, for causing RF current to flow between said cardiac location and said electrically conductive plate, resulting in ablation of cardiac material at said cardiac location, but not at said electrically conductive plate.

6. A method according to claim 5, wherein said step of locating an electrically conductive plate includes the step of locating an electrically conductive back plate adjacent to the back of said patient.

7. A method according to claim 6, wherein said step of locating an electrically conductive back plate adjacent to, and in close proximity to with, the back of said patient, includes the step of making galvanic contact between said back plate and said back of said patient.

8. A method according to claim 6, wherein said step of locating an electrically conductive back plate precedes said step of inserting a catheter arrangement.

9. A method according to claim 5, wherein said step of connecting said action potential sensing means precedes said step of inserting said catheter arrangement.

10. A method according to claim 5, further comprising the steps of:

removing said first catheter body from said guide wire, while said enlarged distal portion of said guide wire remains in said particular cardiac location; and slipping over said guide wire, from said proximal end of said guide wire, the distal end of a guide-wire lumen of a second catheter body separate from said first catheter body, (a) said guide-wire lumen of said second catheter body extending from a location near said proximal end to said distal end of said second catheter body, said guide-wire lumen of said second catheter body having a transverse dimension throughout a principal portion of its length which is selected to accommodate said guide wire, (b) said guide-wire lumen of said second catheter body also having a predetermined diameter at said distal end of said second catheter body, which may be greater than said transverse dimension of said guide-wire lumen of said second catheter body, (c) said second catheter body further including a flexible, electrically conductive sheath electrically insulated from, and surrounding, said guide-wire lumen of said second catheter body, and extending from a location near said distal end of said second catheter body to a location near said proximal end of said second catheter body, and including electrical connection means located near said proximal end of said body of said second catheter body, for forming, in conjunction with said guide wire, an unbalanced transmission line by which RF energy may be guided.

11. A method according to claim 10, wherein said step of removing said first catheter body from said guide wire includes the step of disconnecting said action potential sensing means from at least said guide wire.

12. A sensing and ablation arrangement for performing cardiac ablation on a patient, said sensing and ablation arrangement comprising:

(A) an electrically nonconductive elongated catheter body defining proximal and distal ends; said catheter body including (a) a guide-wire lumen extending from a location near said proximal end to said distal end of said catheter body, said guide-wire lumen having a particular transverse dimension throughout a principal portion of its length which is selected to accommodate a guide wire, said guide-wire lumen also having a predetermined diameter at said distal end, which may be greater than said particular transverse dimension of said guide-wire lumen;

(b) an exposed electrically conductive first electrode located near said distal end of said catheter body; and (c) electrical terminus means located near said proximal end of said catheter body, for making electrical connections thereto; and (d) elongated electrical conducting means extending from said electrical terminus means to said first electrode, and in galvanic electrical communication therewith; said catheter further comprising:

(B) an electrically conductive guide wire longer than said catheter body, said guide wire including an elongated body portion extending through said guide-wire lumen of said catheter in a manner axially movable in relation thereto, and in a manner such that said guide wire and said catheter body can be completely separated from each other, said guide wire further comprising an enlarged distal end portion larger than said predetermined diameter, whereby the distal end of said guide-wire lumen is occluded when said guide-wire is fully retracted with said enlarged distal end portion abutting said distal end of said guide-wire lumen;

(C) action potential sensing means coupled to said proximal end of said guide wire and to said electrical terminus means, for sensing action potentials appearing between said enlarged end portion of said guide wire and said first electrode, whereby said enlarged end portion of said guide wire may be moved to a cardiac location identifiable by said action potentials;

(D) RF signal generating means coupled to said proximal end of said guide wire, for causing RF signal energy to be guided to said cardiac location, for causing RF current to flow through said enlarged distal end portion of said guidewire at said cardiac location, resulting in ablation of cardiac material at said cardiac location.

13. An arrangement according to claim 12, further comprising:

an electrically conductive contact plate located adjacent to, and in contact with, the exterior of said patient, said contact plate having a surface area greater than that of said enlarged distal end portion of said guide-wire;

RF signal coupling means coupled to said contact plate and to said RF signal generating means, for causing said RF current to flow between said enlarged distal end portion of said guidewire and said contact plate, whereby said ablation takes place at said cardiac location, but not at said contact plate.

14. An arrangement according to claim 13, wherein said contact plate is a back plate.

15. An arrangement according to claim 12, wherein at least a distal portion of said body portion of said guide wire is surrounded by electrical insulation, leaving at least a distal portion of said enlarged distal end portion of said guide wire exposed.

16. An arrangement according to claim 12, further comprising:

(A) a second catheter body separate from said first-mentioned catheter body, said second catheter body including a guide-wire lumen extending from a location near said proximal end to said distal end of said second catheter body, said guide-wire lumen of said second catheter body having a transverse dimension throughout a principal portion of its length which is selected to accommodate said guide wire, said guide-wire lumen of said second catheter body also having a predetermined diameter at said distal end of said second catheter body, which may be greater than said transverse dimension of said guide-wire lumen of said second catheter body;

(B) a flexible, electrically conductive sheath electrically insulated from, and surrounding, said guide-wire lumen of said second catheter body, and extending from a location near said distal end of said second catheter body to a location near said proximal end of said second catheter body, and including electrical connection means located near said proximal end of said body of said second catheter body, for forming, in conjunction with said guide wire, an unbalanced transmission line by which said RF energy may be guided; and (C) electrical insulation means surrounding said sheath over a principal portion of said second catheter body, for insulating said patient from galvanic contact with said sheath.

17. An arrangement according to claim 16, wherein said RF signal generator is coupled to said proximal end of said guidewire and to said electrically conductive sheath.

* * * * *